US006585738B1

(12) United States Patent
Mangione et al.

(10) Patent No.: US 6,585,738 B1
(45) Date of Patent: Jul. 1, 2003

(54) SPINAL OSTEOSYNTHESIS DEVICE FOR ANTERIOR FIXATION WITH PLATE

(75) Inventors: Paolo Mangione, Pessac (FR); Régis Le Couëdic, Cestas (FR); Denis Pasquet, Bordeaux (FR); Frédéric Conchy, Saint -Médard- d'Eyrans (FR)

(73) Assignee: Stryker Spine (FR)

( * ) Notice: Subject to any disclaimer, the term of this patent is extended or adjusted under 35 U.S.C. 154(b) by 0 days.

(21) Appl. No.: 09/743,146

(22) PCT Filed: Apr. 27, 1999

(86) PCT No.: PCT/FR00/00994

§ 371 (c)(1),
(2), (4) Date: May 16, 2001

(87) PCT Pub. No.: WO00/01314

PCT Pub. Date: Jan. 13, 2000

(30) Foreign Application Priority Data

Jul. 6, 1998 (FR) .............................................. 98 08602

(51) Int. Cl.[7] .......................... A61B 17/56; A61B 17/58; A61F 2/30
(52) U.S. Cl. ............................... 606/61; 606/60; 606/71
(58) Field of Search ............................... 606/61, 69, 70, 606/71

(56) References Cited

U.S. PATENT DOCUMENTS

| 5,324,290 A | * | 6/1994 | Zdeblick et al. | 606/61 |
| 5,470,333 A | * | 11/1995 | Ray | 606/61 |
| 5,549,607 A | * | 8/1996 | Olson et al. | 606/61 |
| 5,601,554 A | * | 2/1997 | Howland et al. | 606/61 |
| 5,980,523 A | * | 11/1999 | Jackson | 606/61 |
| 6,238,396 B1 | * | 5/2001 | Lombardo | 606/61 |
| 6,331,179 B1 | * | 12/2001 | Freid et al. | 606/61 |
| 6,402,756 B1 | * | 6/2002 | Ralph et al. | 606/71 |

FOREIGN PATENT DOCUMENTS

| EP | 0 556 548 A1 | 8/1993 |
| FR | 2 651 992 | 3/1991 |
| FR | 2 766 353 | 1/1999 |
| WO | 94/20048 | 9/1994 |

* cited by examiner

Primary Examiner—David J. Walczak
Assistant Examiner—Amanda Flynn
(74) Attorney, Agent, or Firm—Lerner, David, Littenberg, Krumholz & Mentlik, LLP

(57) ABSTRACT

A backbone osteosynthesis system for anterior fixing comprising first and second arms, each capable of receiving bone screws and a longitudinal plate for rigidly linking the arms, the plate being in one single piece with the first arm. The system comprises a way to adjust the second arm in a longitudinal position on the plate.

24 Claims, 4 Drawing Sheets

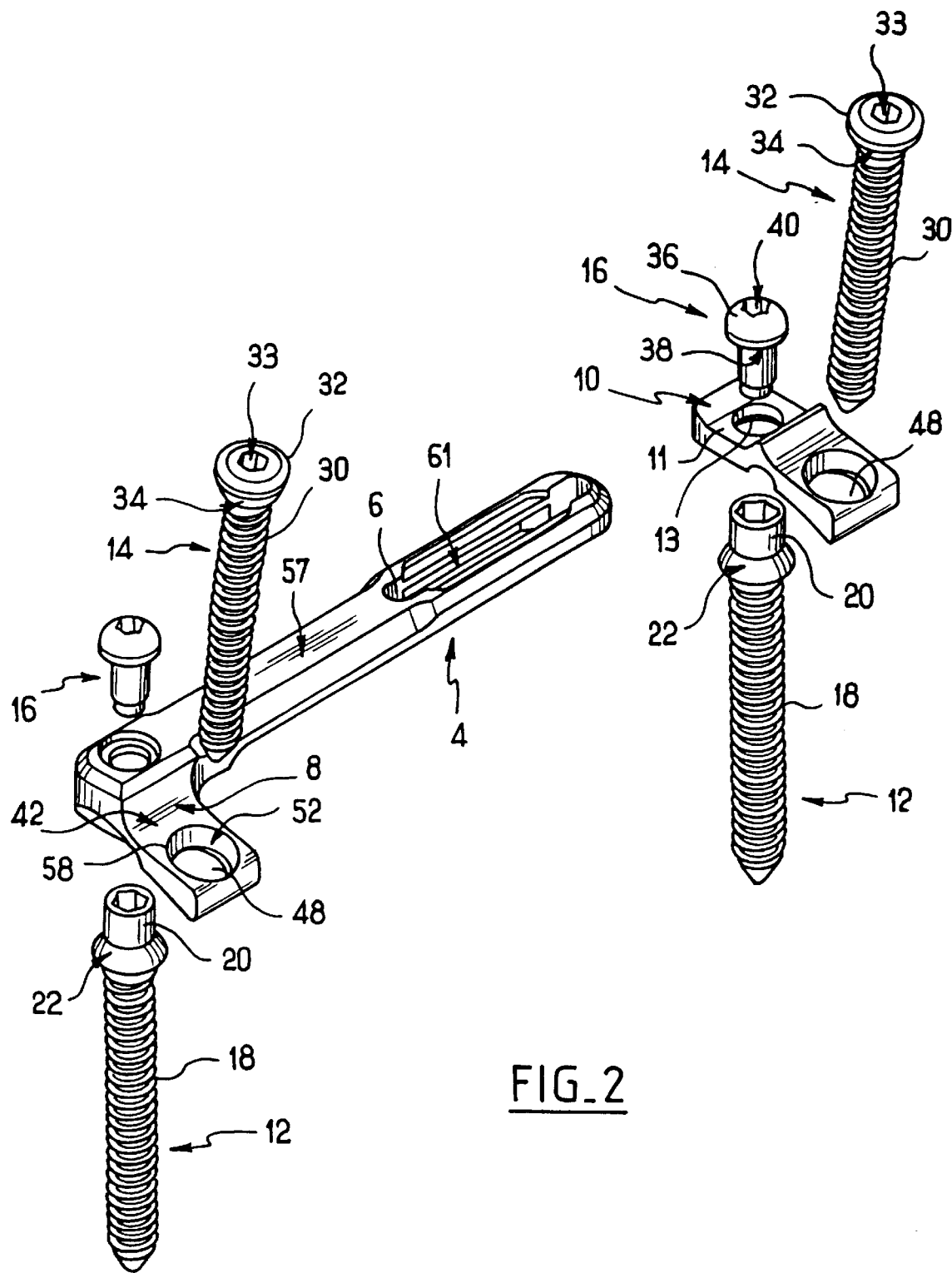
FIG_2

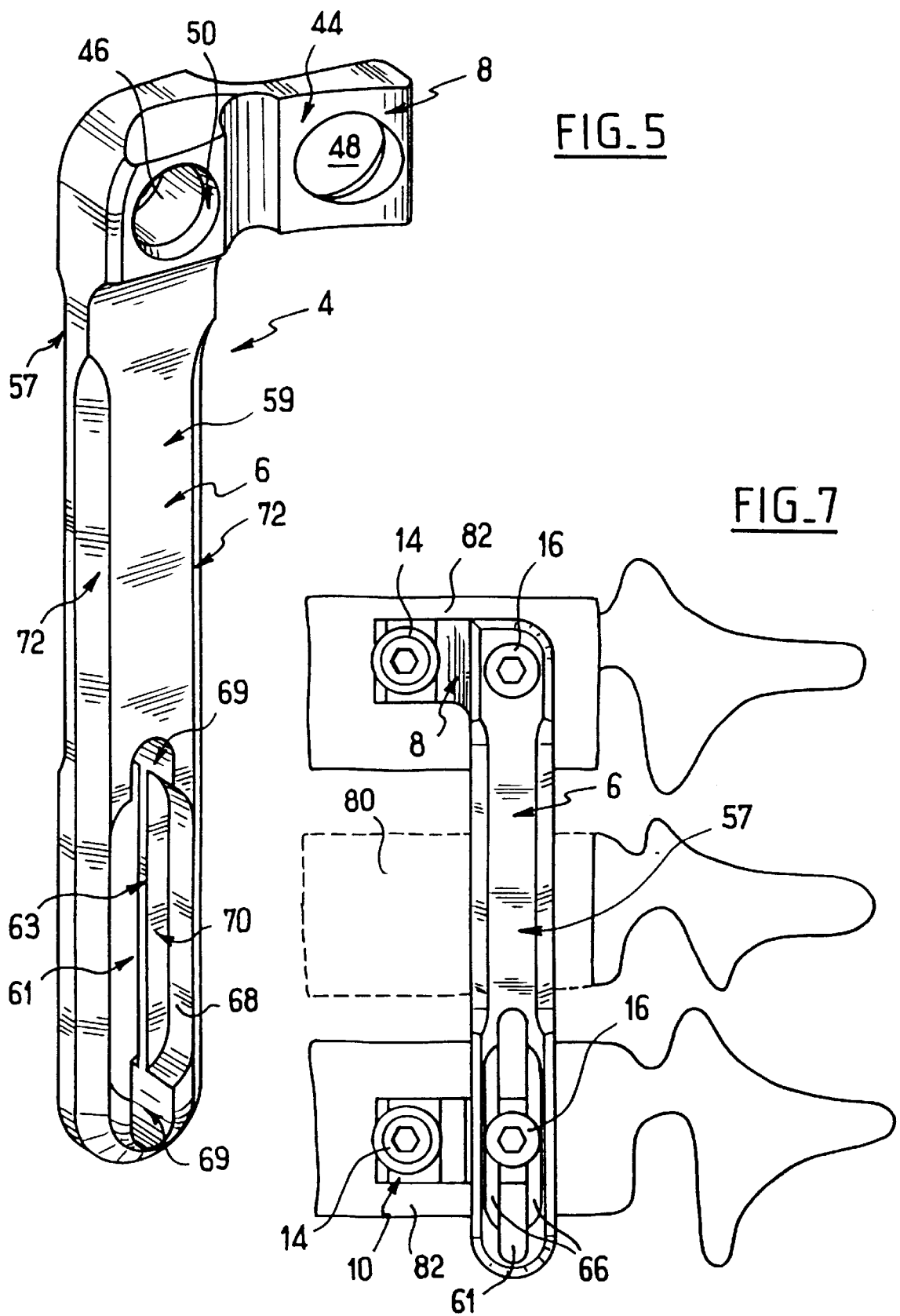

SPINAL OSTEOSYNTHESIS DEVICE FOR ANTERIOR FIXATION WITH PLATE

BACKGROUND OF THE INVENTION

The invention concerns spinal osteosynthesis systems, in particular for anterior fixation.

A spinal osteosynthesis system for anterior fixation is known from the document WO 94/06360. Said system includes a longitudinal plate and one arm made in one piece with the plate, extending from one end of the latter and inclined relative to its longitudinal direction. This arm receives two bone screws to be anchored in a vertebra. The other end of the plate has two oblong orifices parallel with each other and intended to receive two respective bone screws to be anchored in another vertebra. The two fixation vertebrae are separated by the vertebra intended for arthrodesis. The oblong orifices make it possible to adjust the longitudinal position of the two screws relative to the arm. As the number of components to be assembled is limited, this system can be fitted quickly during an intervention. However, the main component of this system is bulky, which makes it difficult to introduce into the body by the endoscopic route. Moreover, this main component is not designed to be adapted to the configuration of the patient's vertebrae with a view to optimizing its position or the quality of its fixation to the vertebrae.

SUMMARY OF THE INVENTION

An object of the invention is to provide a system which at one and the same time is quicker to fit and is easy to introduce by the endoscopic route.

To achieve this object, the invention provides a spinal osteosynthesis system for anterior fixation, comprising first and second arms which can each receive bone screws, and a longitudinal plate which can rigidly link the arms, the plate being made in one piece with the first arm, and the system comprising means for adjusting a longitudinal position of the second arm on the plate.

Thus, with the second arm being separable from the plate, the system is made up of elements which are small in size and can be introduced into the body by the endoscopic route as well as by the normal route. Disregarding the screws, the essential elements of the system are two in number, so that installation of the system (assembly and relative positioning of the components) in the body is a simple matter. The operating time thus remains short. The presence of the plate made in one piece with the first arm makes it possible to envisage reducing very substantial kyphosis by the anterior route by means of leverage on the vertebra associated with this arm. Moreover, the plate can be placed in the most posterior position possible on the vertebral body, allowing free access to the damaged vertebra or to the graft. Finally, with a view to adapting it to the configuration of the vertebrae, the second arm can be easily shaped since it is independent of the rest oft he system.

The invention may advantageously present one or more of the following characteristics:

- the plate has at least one orifice for adjusting the longitudinal position;
- the orifice is of oblong shape;
- the orifice has, at least one end, a continuation with a width smaller than the width of a central part of the orifice;
- the system includes an adjusting or fixation screw which can be fixed to the second arm and can slide in the orifice;
- the system comprises at least one fixation screw which can be engaged in one of the bone screws associated with one of the arms, in order to fix the arm to the bone screw;
- the arm has an orifice which can be interposed between the bone screw and the fixation screw;
- the fixation screw is the adjusting screw;
- the second arm and the plate have centering faces which can come into mutual contact in order to center the arm relative to the plate;
- the arm and the plate each have two centering faces which can form a male-female assembly;
- the centering faces are plane;
- each arm can be bent manually.

Other characteristics and advantages of the invention will also become apparent from the following description of a preferred embodiment given as a nonlimiting example. In the attached drawings:

FIGS. 1 and 2 are two perspective views, in the assembled state and the disassembled state, respectively, of a preferred embodiment of the osteosynthesis system according to the invention;

FIG. 5 is a perspective view of the element constituting the plate and the first arm of the system in FIG.

FIG. 7 shows the system in FIG. 1 fitted on vertebrae.

Figure 1:
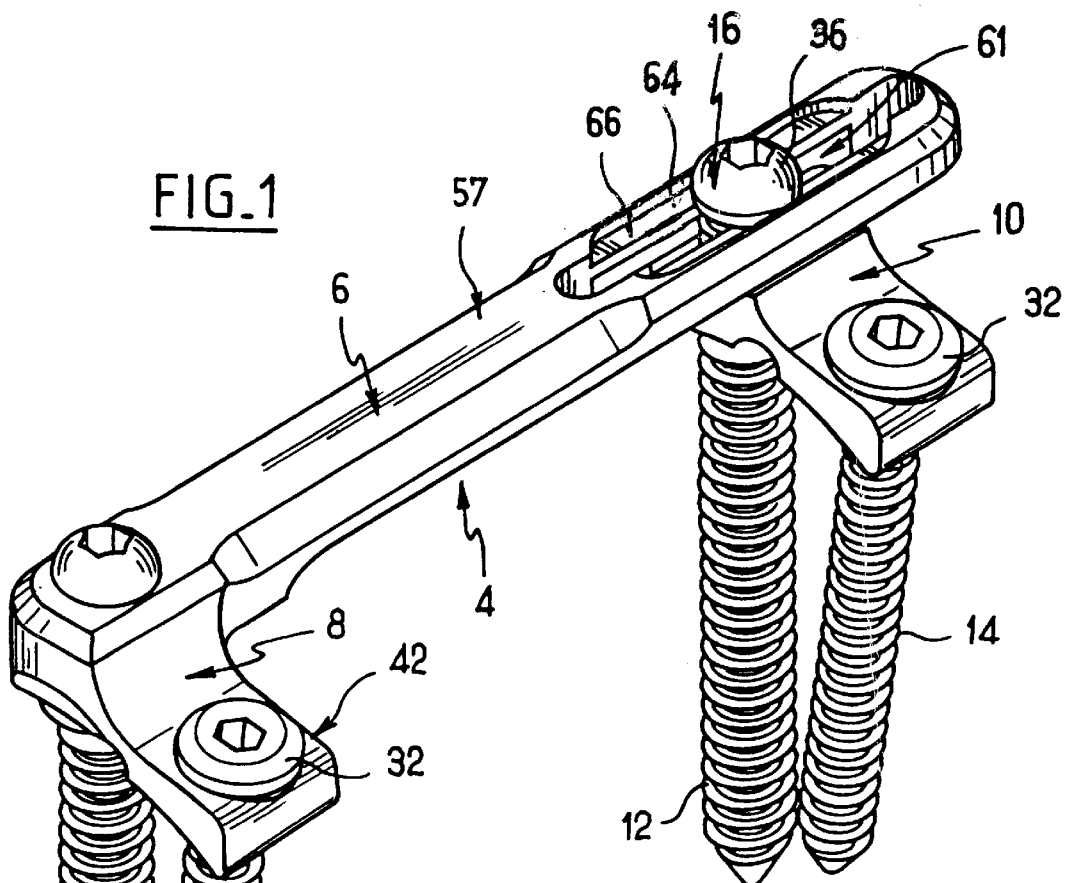

The spinal osteosynthesis system for anterior fixation according to the invention includes, in the present embodiment, an element 4 in one piece forming plate 6 and first arm 8. LD The system includes a second arm 10 and, for each arm 8, 10, two primary 12 and secondary 14 vertebral anchoring screws, and also a clamping or fixation screw 16. The two primary screws 12 are identical to each other, as are the two secondary screws 14 and the two fixation screws 16.

It will be noted that the secondary screws can in practice be identical or different, depending on the surgeon's choice.

Figure 6:
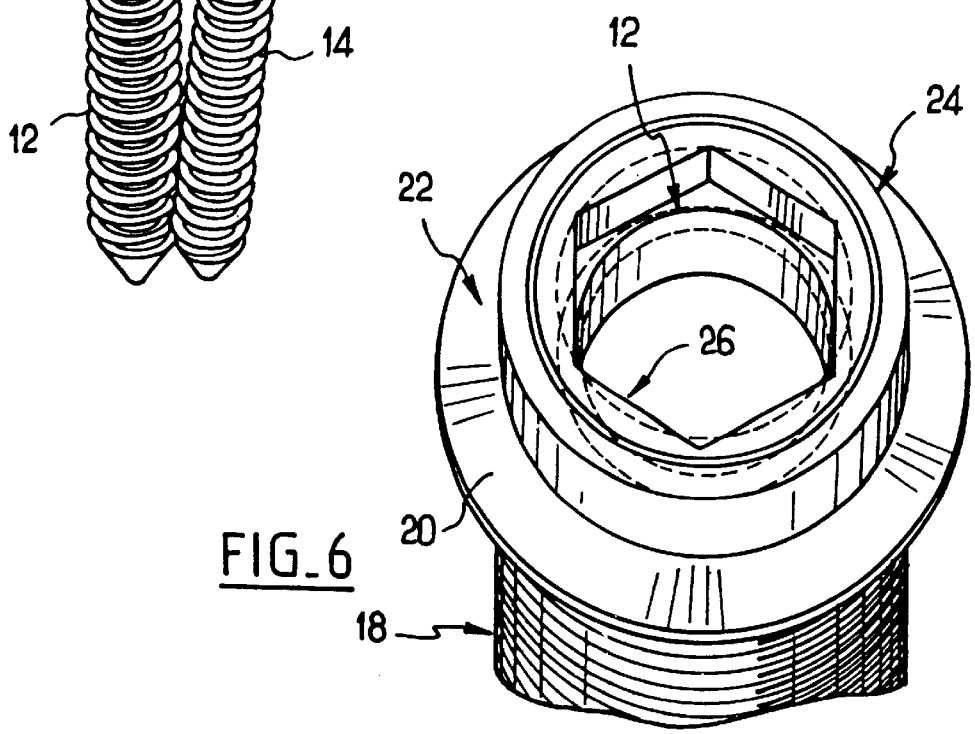
FIG. 6 is a perspective view of the head of one of the primary anchoring screws.

Each primary screw 12 has a threaded cylindrical body 18. It is self-tapping and bicortical. The body is provided with a bone threading. The screw has a head 20 and, between the body and the head, a flange having an upper face 22 of frustoconical shape narrowing in the direction of the head. Referring in particular to FIG. 6, the head 20 of the screw has a smooth cylindrical outer face 24 and an inner face 26 of hexagonal socket shape in which a thread is cut. The hexagonal recess allows the screw to be rotated by means of a tool.

In an alternative embodiment, the screw does not have the hexagonal recess and instead only has a thread formed in a cylindrical inner face. Moreover, the flange this time has a hexagonal shape, or else has two flats parallel to the axis of the screw, parallel to each other and diametrically opposite each other with a view to engaging with a tightening wrench, or any other means for rotating the primary screw.

Each secondary screw 14 is self-tapping and monocortical (or alternatively bicortical). It has a threaded cylindrical body 30 with a bone threading. It comprises a head 32 which has, in its upper face, a hexagonal recess 33 or recess of any other shape able to engage with a tightening tool such as a wrench or a screwdriver. The head has a lower face 34 contiguous with the body and of spherical shape.

Each fixation screw 16 has a threaded cylindrical body which can constitute a screw-nut connection with the head of the associated primary screw 12. The fixation screw 16 comprises a head 36 having a plane lower face 38 perpendicular to the axis of the screw. The head 36 has, on its upper face, a recess 40 of the abovementioned type, designed to engage with a tightening tool.

Figure 3:
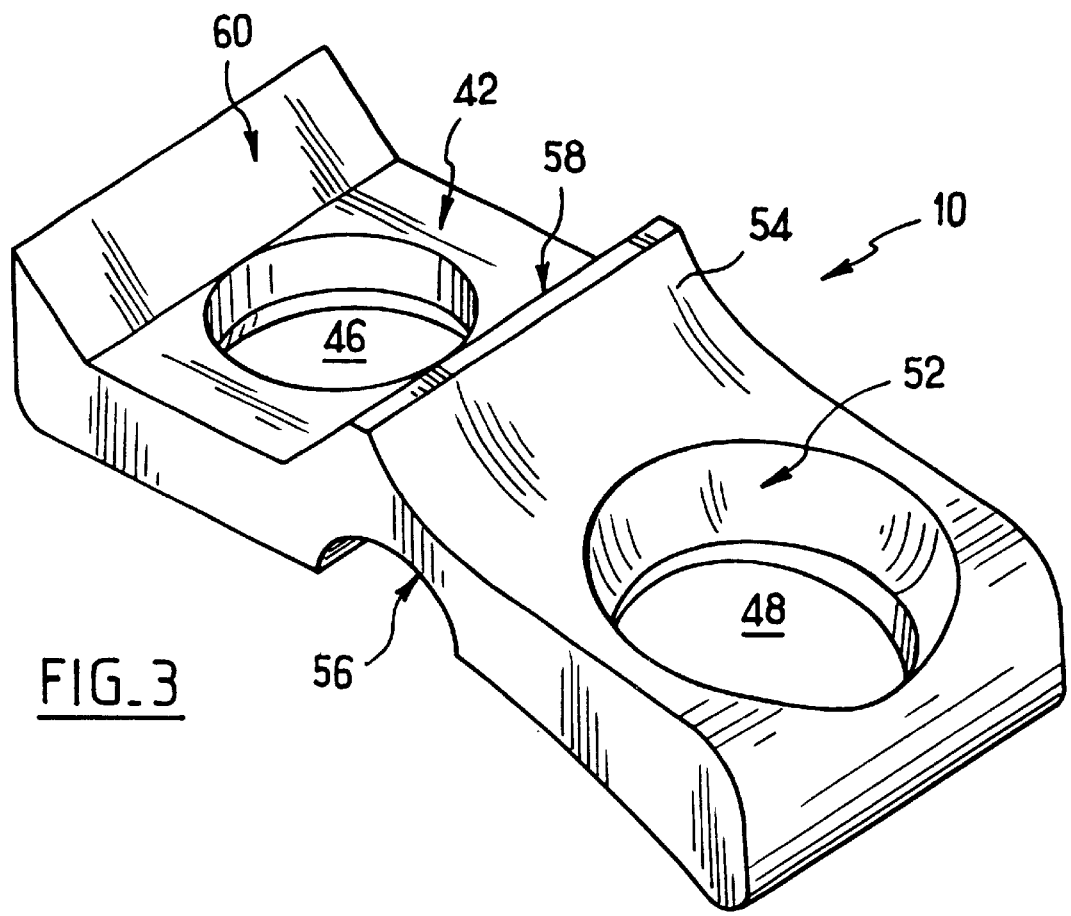
FIGS. 3 and 4 are two perspective views, from above and from below, respectively, of the second arm of the system in FIG. 1.
Figure 4:
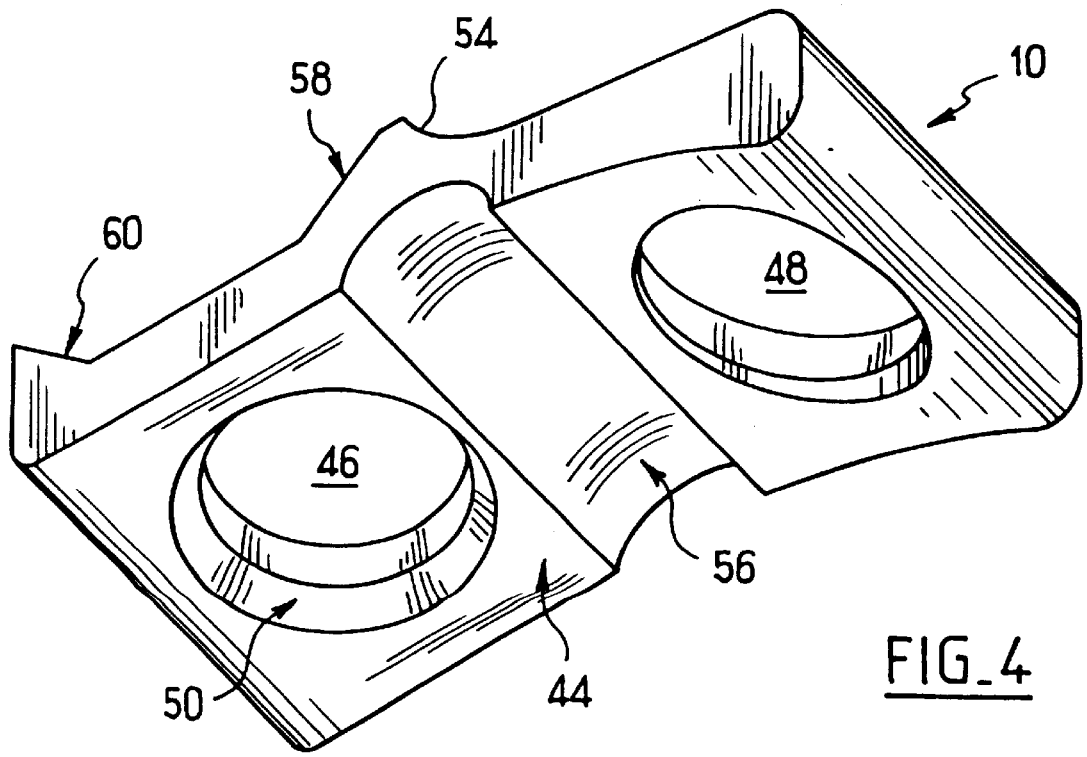

Referring to FIGS. 3 and 4, the second arm or connector 10 has a generally flat rectangular shape defining two plane faces, namely upper plane face 42 and lower plane face 44, which are generally parallel to each other. The arm has first and second circular orifices 46, 48. The upper face 42 serves, in the vicinity of the first orifice 46, as a plane bearing for the lower face 38 of the associated fixation screw 16, in order to make surface contact with the latter and lock it by friction so as to clamp it. The lower edge 50 of this orifice has a frustoconical shape which can form a surface contact with the frustoconical face 22 of the flange of the primary screw 12. The second orifice 48 has an upper edge 52 of spherical shape which can come into contact with the spherical lower face 34 of the secondary screw 14 with a view to adjusting the position of the secondary screw by varying its angle in its seat formed by the orifice 48.

The upper face 42 of the second arm has a rib 54 extending between the two orifices 46, 48, perpendicular to the longitudinal direction of the arm, and dividing this face into two substantially equal parts. Approximately in line with this rib 54, the lower face 44 has a profiled channel 56 of circular cross section, nearer to the second orifice 48 than to the first orifice 46, so that it constitutes a local thinning of the arm, making it capable of being bent manually during a surgical intervention. Opposite the first orifice 46, the groove 54 has a plane bevel 58 inclined relative to the face 42. At an end edge adjacent to the first orifice, the arm has a border forming a second plane bevel 60 inclined relative to the face 42, opposite the first orifice. The two bevels 58, 60 extend opposite each other in a common transverse direction and define in a section a female trapezoidal shape.

Referring to FIG. 5, on the element 4 the first arm 8 is identical to the second arm 10 except for the fact that the recess formed by the two bevels 58, 60 and the portion of the upper face 42 between these is absent. The plate has a generally elongate, rectilinear flat shape. The first arm 8 and the plate 6, which here extend perpendicular to each other, give the element 4 a general L shape. One end of the first arm 8 extends at a first end of the plate 6.

The plate 6 has an upper face 57 and a lower face 59 which are parallel to each other. The plate 6 has an oblong orifice 60 extending parallel to a longitudinal direction of the plate. The orifice has plane edges 63 parallel to each other. On a central portion of the orifice, over a length greater than half or three quarters of the orifice, the edges 63 have respective recesses 64 on each side of the orifice, adjacent to the upper face 57, each one forming a plane face 66 parallel to the upper face and a plane face perpendicular thereto and parallel to the longitudinal direction of the plate. On the lower face 59, the plate is provided, adjacent to the lower face 59 of the plate, with analogous recesses 68, with faces 70. The ends of the orifice extend beyond these recesses 64, 68 and constitute continuations 69 having a width smaller than the central width of the orifice measured in the area of the recesses 64, 68. The plate 6 has two plane bevels 72 formed on the longitudinal edges of the lower face 59. In cross section, these bevels 72 and the lower face constitute a male trapezoidal shape.

Upon installation, a male-female assembly is obtained via the bevels 58, 60 of the second arm 10 which receives the bevels 72 of the plate from above, thus forming, in a pair, a surface contact which ensures centering of the second arm relative to the plate across the width of the plate. The four bevels are dimensioned in such a way that an interstice is formed, even after locking, between the lower face 59 of the plate and the upper face 42 of the second arm which do not come into contact. This thereby guarantees cooperation along oblique lines of force which induce a slight elastic deformation of the materials in the area of the contacting bevels and, consequently, substantial stresses. Under these conditions, the friction between the bevels is sufficient to ensure stable locking, in the longitudinal position, of the second arm relative to the plate.

The head of the main screw 12 is introduced from below into the first orifice 46 of the second arm 10, then from below into the oblong orifice 61 of the plate. The fixation screw 16 is engaged from above in the head of the main screw 12. Its plane lower face 38 comes into surface contact, at any position, against the plane face 66 of the recesses 64 in order to establish effective clamping. It is therefore possible to select the longitudinal position of the second arm 10 along the oblong orifice of the plate 6.

The frustoconical face 20 of the main screw 12 comes into surface contact against the frustoconical edge 50 of the second arm 10 for rigidly locking the screw relative to the arm. Referring to FIG. 7, Ian a surgical intervention, after exposing the affected vertebra 80 and the two adjacent vertebra 82, vertebrectomy is performed, with preservation, if possible, of the respective endplates of these vertebrae. A pilot hole is formed on the lateral aspect of the vertebra 82 at an equal distance from the upper and lower endplates, and at the limit of the most posterior quarter of the vertebral body. A primary screw 12 is then introduced into this pilot hole as far as the limit flange. The second arm 10 is then positioned on the latter. The frustoconical faces 20, 50 come into mutual contact, and the conformity of the second arm 10 to the associated vertebra 82 is examined and can be modified by withdrawing the second arm and bending if manually. The secondary screw 14 is then screwed into the second orifice 48 of the second arm 10 until its spherical face 34 comes into contact with that 52 of the second arm. It is preferable to position the second arm 10 as parallel as possible to the endplates. The elements 4 is fixed in the same way by means of the first arm 8.

After the two adjacent vertebrae 82 have been thus equipped, the plate 50 is positioned in the second arm 10. Final clamping is effected by means of the fixation screw 16 introduced, as has been explained above, into the primary screw 12 of the second arm 10. Contraction or distraction can be performed beforehand, in order to achieve the desired distance, with the aid of distraction forceps whose ends can be received in the continuations 69 of the oblong orifice 61.

Although the invention herein has been described with reference to particular embodiments, it is to be understood that these embodiments are merely illustrative of the of principles and applications of the present invention. It is therefore to be understood that numerous modifications may be made to the illustrative embodiments and that other arrangements may be devised without departing from the spirit and scope of the present invention as defined by the appended claims.

What is claimed is:

1. A spinal osteosynthesis system for anterior fixation, comprising first and second arms, which can each receive bone screws and a longitudinal plate which can rigidly link the arms, the plate being made in one piece with the first arm and means for adjusting a longitudinal position of the second arm on the plate said means including a vertebral screw for coupling said second arm to said plate.

2. The system according to claim 1 wherein the plate has at least one orifice for adjusting the longitudinal position.

3. The system according to claim 2 wherein the orifice is of oblong shape.

4. The system according to claim 3 wherein the orifice has, at at least one end, a continuation with a width smaller than the width of a central part of the orifice.

5. The system according to claim 3 or 4 further including a fixation screw which can be fixed to the second arm and can slide in the orifice.

6. The system according to claim 1 further comprising at least one fixation screw which can be engaged in one of the bone screws associated with at least one of the arms in order to fix the arm to the bone screw.

7. The system according to claim 6 wherein said at least one arm has an orifice which can be interposed between the bone screw and the fixation screw.

8. The system according to claims 6 or 7 wherein the fixation screw is an adjusting screw.

9. The system according to claim 1 wherein the second arm and the plate have centering faces which can come into mutual contact in order to center the arm relative to the plate.

10. The system according to claim 9 wherein the second arm and the plate each have two centering faces which can form a male-female assembly.

11. The system according to claim 9 or 10 wherein the entering faces are planar.

12. The system according to claim 1 wherein each arm can be bent manually.

13. A spinal plating system comprising:
   an elongated bone plate having a longitudinal axis and a bone screw receiving opening at a first end and a longitudinally extending slot at a second end;
   a bone screw slidingly engaging said slot; and
   an arm element slidably received on said plate adjacent said slot, said arm element having an opening thereon for receiving said bone screw engaging said slot, said arm element having a locking portion for lockingly engaging said bone plate to lock said arm element and said bone screw at a selected longitudinal location with respect to said slot.

14. The spinal plating system as set forth in claim 13 wherein said arm element has a portion extending transversely to the longitudinal axis of said plate, said portion including an opening for receiving a bone screw.

15. The spinal plating system as set forth in claim 14 wherein said locking portion on said arm element is a recess having a pair of tapered sidewalls for wedging engagement with tapered sidewalls of said bone plate.

16. The spinal plating system as set forth in claim 15 wherein said bone screw for slidably engaging said slot has a first part with a threaded shank and a head with a threaded bore and a second part in the form of a clamping element having a threaded shank for engaging the threaded bore in said head, said head having a surface for engaging a surface of said arm element around said opening and said clamping element having a surface for engaging said bone plate adjacent said slot.

17. The spinal plating system as set forth in claim 14 wherein said first end of said bone plate has a portion extending transversely to said longitudinal axis, said portion including an opening for receiving a bone screw.

18. The spinal plating system as set forth in claim 17 wherein said portion of said arm element extending transversely to said bone plate is connected to said locking portion by a section having a reduced cross-section to allow said transversely extending portion to deform with respect to said locking portion.

19. A spinal osteosynthesis system for anterior fixation, comprising first and second arms, which can each receive bone screws and a longitudinal plate which can rigidly link the arms, the plate being made in one piece with the first arm and means for adjusting a longitudinal position of the second arm on the plate and further comprising at least one fixation screw which can be engaged in one of the bone screws associated with one of the arms in order to fix the arm to the bone screw.

20. A method for connecting two vertebra comprising:
   attaching a first part of a two piece first bone screw into a first vertebra, the first bone screw part having a head with a threaded bore;
   attaching a first part of a two piece second bone screw into a second vertebra, the second bone screw first part having a head with a threaded bore; and
   attaching an elongated bone plate having a longitudinal axis and a screw receiving opening for said first bone screw at a first end and a longitudinally extending slot at a second end for receiving said second bone screw to the first and second vertebra by placing said plate on said first and second bone screw first parts and attaching a clamping element to said first and second bone screws by inserting a threaded shank on clamping elements through said screw receiving opening and said slot in said plate, into said threaded bore in said bone screw heads and clamping said plate to said screw first parts.

21. The method as set forth in claim 20 further comprising:
   attaching an arm element to said bone plate by placing said arm, element between said second screw first part and said plate prior to clamping said plate to said second screw first part with said clamping element.

22. The method as set forth in claim 21 further comprising placing an additional screw into said second vertebra through a portion of said arm element extending transversely to the longitudinal axis of said plate.

23. The method as set forth in claim 22 further comprising bending said transversely extending portion of said arm element so that a surface thereof contacts said second vertebra.

24. The method as set forth in claim 21 further including locking the arm element to the plate by the engagement of tapered male and female surfaces on said plate and said arm element.

* * * * *

UNITED STATES PATENT AND TRADEMARK OFFICE
CERTIFICATE OF CORRECTION

PATENT NO. : 6,585,738 B1
DATED : July 1, 2003
INVENTOR(S) : Paolo Mangione et al.

It is certified that error appears in the above-identified patent and that said Letters Patent is hereby corrected as shown below:

Column 1,
Line 55, "oft he" should read -- of the --.

Column 2,
Line 28, after "Fig." insert -- 1. --.
Line 35, delete "LD".

Column 4,
Line 41, "is" should read -- are --.
Line 53, "after "the" delete "of".
Line 66, after "plate" insert -- , " --.

Column 5,
Line 8, "claim" should read -- claims --.
Line 27, "entering" should read -- centering --.

Column 6,
Line 42, after "arm" delete ",".

Signed and Sealed this

Fourth Day of November, 2003

JAMES E. ROGAN
*Director of the United States Patent and Trademark Office*